(12) United States Patent
Zhao

(10) Patent No.: US 8,722,697 B2
(45) Date of Patent: May 13, 2014

(54) PHARMACEUTICAL COMPOSITION FOR TREATING HYPERTENSION AND METABOLIC SYNDROME AND USE THEREOF

(75) Inventor: Zhiquan Zhao, Linyi (CN)

(73) Assignee: Lunan Pharmaceutical Group Corporation, Linyi, Shandong Province (CN)

( * ) Notice: Subject to any disclaimer, the term of this patent is extended or adjusted under 35 U.S.C. 154(b) by 179 days.

(21) Appl. No.: 13/055,175

(22) PCT Filed: Jul. 23, 2009

(86) PCT No.: PCT/CN2009/000824
§ 371 (c)(1),
(2), (4) Date: Jan. 21, 2011

(87) PCT Pub. No.: WO2010/009619
PCT Pub. Date: Jan. 28, 2010

(65) Prior Publication Data
US 2011/0130416 A1    Jun. 2, 2011

(30) Foreign Application Priority Data

Jul. 24, 2008  (CN) .......................... 2008 1 0133753

(51) Int. Cl.
*A01N 43/54*     (2006.01)
*A61K 31/505*    (2006.01)

(52) U.S. Cl.
USPC ........................................................ 514/275

(58) Field of Classification Search
CPC . A61K 9/1652; A61K 9/2054; A61K 9/2059; A61K 9/209; A61K 9/4866; A61K 31/4422; A61K 31/4439; A61K 31/505; A61K 2300/00
USPC .......................................... 424/400; 514/275
See application file for complete search history.

(56) References Cited

U.S. PATENT DOCUMENTS

| 2009/0054473 A1 * | 2/2009 | Roden et al. ................... 514/274 |
| 2010/0048644 A1 * | 2/2010 | Xu et al. ........................ 514/356 |

FOREIGN PATENT DOCUMENTS

| CN | 1762361 | 4/2006 |
| CN | 200610028434.8 | 6/2006 |
| CN | 101229372 | 7/2008 |
| WO | WO 2008052431 A1 * | 5/2008 |

OTHER PUBLICATIONS

Ansell, Benjamin J. (2005). "Rationale for Combination Therapy with Statin Drugs in the Treatment of Dyslipidemia". Current Atherosclerosis Reports, 7: 29-33.*
Israili et al (2006) "Metabolic syndrome;treatment of hypertensive patients with this syndrome." Retrieved on Jul. 31, 2013. Retrieved from the internet <URL: http://www.redalyc.org/articulo.oa?id=170217081002>.*
ACTOS prescribing information. Retrieved on Jul. 31, 2013. Retrieved from the Internet <URL: http://dailymed.nlm.nih.gov/dailymed/archives/fdaDrugInfo.cfm?archiveid=9949>.*
NORVASC prescribing information. Retrieved on Jul. 31, 2013. Retrieved from the Internet <URL: http://labeling.pfizer.com/ShowLabeling.aspx?id=562.*
CRESTOR prescribing information. Retrieved on Jul. 31, 2013. Retrieved from the Internet <URL: http://www.accessdata.fda.gov/drugsatfda_docs/label/2009/021366s015lbl.pdf.*
Zhao et al (2003) "Study of protein binding of amlodipine and levamlodipine in human plasma albumin and bovine serum albumin solution by high performance capillary electrophoresis frontal analysis". Retrieved on Jul. 31, 2013. Retrieved from the internet <URL: http://china.chemistrymag.org/cji/2003/051004pe.htm>.*
International Search Report, Application No. PCT/CN2009/000824, mailed Nov. 5, 2009.
Yin et al.; "The Curative Effect of Using Sinvastatin, Pioglitazone Hydrochloride and Levamlodipine Besylate Jointly to Treat the Metabolic Syndrome"; West China Medical Journal (Chinese); May 2009; vol. 24, No. 5, pp. 1122-1124.
Zhang et al.; "Progress of Blood Pressure Lowering Drugs not Considered Antihypertensives"; Adv. Cardiovasc Dis (Chinese); Nov. 2008; vol. 29, No. 6, pp. 953-956.
Yang et al.; "Drug Usage of Compound Preparation for Hypertension"; Chin J of Clinical Rational Drug Use (Chinese); May 2009; vol. 2, No. 9, pp. 31-33.
Martin-Ventura et al., "Treatment with amlodipine and atorvastatin has additive effect on blood and plaque inflammation in hypertensive patients with carotid atherosclerosis", Kidney International, 2008, vol. 74 (Suppl. 111), pp. S71-S74.

* cited by examiner

*Primary Examiner* — Robert T Crow
*Assistant Examiner* — Doan Phan
(74) *Attorney, Agent, or Firm* — Renner, Otto, Boisselle & Sklar, LLP

(57) ABSTRACT

The present invention provides a pharmaceutical composition comprising the following active ingredients: 1) amlodipine or a pharmaceutically acceptable salt thereof, 2) pioglitazone or a pharmaceutically acceptable salt thereof, and 3) rosuvastatin or a pharmaceutically acceptable salt thereof. The present invention also provides use of the pharmaceutical composition in preparing a medicament for treating hypertension or metabolic syndrome. The pharmaceutical composition of the present invention can treat hypertension or metabolic syndrome, while effectively controlling the incidence of associated cardiovascular diseases and more potently improving survival prognosis in hypertensive patients. When blood pressure is lowered to desired level, the risk factors such as cardiovascular diseases are rectified, metabolic disorders and prognosis of patients are improved, and survival rate of hypertensive patients is raised.

10 Claims, No Drawings

PHARMACEUTICAL COMPOSITION FOR TREATING HYPERTENSION AND METABOLIC SYNDROME AND USE THEREOF

This application is a national phase of International Application No. PCT/CN2009/000824 filed Jul. 23, 2009.

TECHNICAL FIELD

The present invention relates to the pharmaceutical field, and specifically relates to a pharmaceutical composition and use thereof in preparing a medicament for treating hypertension and metabolic syndrome.

BACKGROUND ART

Hypertension is one of the most common cardiovascular diseases, and is closely related to some of the most fatal human diseases, such as coronary heart disease, cerebrovascular diseases, etc. Although the incidence of hypertension in China is not as high as that in Western countries, it increases year by year. With the improvement of living standards and the degradation of the environment, the number of patients suffered from cardiovascular diseases such as hypertension, hyperlipemia and hypercholesterolemia keeps increasing. According to the report, the number of hypertension patients in China has reached 150 million by the end of 2003, and increases at a rate of 5 million per year. Great attention has been paid all over the world to the researches on hypertension, ranging from pathogenesis to clinical prevention and treatment of the disease. Hypertension mainly impairs the blood vessels of humans, rendering arterial angiosclerosis and arteriarctia, which are generally called "arteriosclerosis". When hypertension is combined with diabetes mellitus, the damage to blood vessels would become accelerated and more severe, and the conditions of patients would be worsened rapidly, to which active treatment should be applied.

Amlodipine is a calcium channel blocker that prevents calcium from transmembranely entering myocardial cells and vascular smooth muscle cells, and thus has anti-hypertension effect. Amlodipine exists as two isoforms, levo-amlodipine and dextro-amlodipine, wherein the activity of levo-amlodipine is 1000 times as high as that of the dextroisomer, and twice as high as that of the racemate. Amlodipine exhibits higher selectivity on vascular smooth muscle than that of nifedipine, and can increase cardiac output and coronary flow of the patients suffered from myocardial ischemia, increase myocardial oxygen supply and decrease oxygen consumption, and improve locomotive ability. Additionally, amlodipine may also activate LDL receptor, reduce the accumulation of fat in artery wall, inhibit the synthesis of collagens, and thus has anti-arteriosclerosis effects. The anti-hypertension effect of amlodipine is based on the mechanism of direct relaxation of the vascular smooth muscle. Although the exact angina-relieving mechanism thereof has not been ascertained, amlodipine can expand peripheral arteriola and coronary artery, reduce peripheral resistance, release coronary artery spasm, decrease cardiac after-load, reduce cardiac energy consumption and oxygen requirement, and thus relieve angina.

Rosuvastatin calcium is a synthesized statin drug which was developed by Shionogi Co., Ltd. (Shionogi Company, Osaka) and assigned to AstraZeneca UK Limited in April, 1998. Rosuvastatin is a selective 3-hydroxyl-3-methylglutaryl-coenzyme A (HMG-CoA) reductase inhibitor, and may be used in the treatment of atheroma, hyperlipemia, familial hypercholesterolemia and similar diseases. The molecular formula of rosuvastatin calcium is shown as follows:

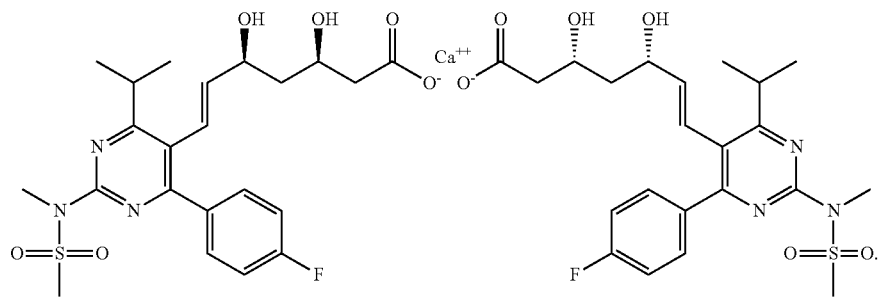 [SMILES: CC(C)c1nc(N(C)S(C)(=O)=O)nc(-c2ccc(F)cc2)c1/C=C/[C@@H](O)C[C@@H](O)CC(=O)[O-] ; [Ca+2] ; CC(C)c1nc(N(C)S(C)(=O)=O)nc(-c2ccc(F)cc2)c1/C=C/[C@@H](O)C[C@@H](O)CC(=O)[O-]]

In view of the clinically testing results and the comparison data among statins, rosuvastatin calcium is indeed a "super statin", which has extremely good antilipemic effects, and is so far the most potent antilipemic drug.

Chinese Patent Application CN200510094723.3 discloses a pharmaceutical composition comprising 5-40 wt. % of amlodipine besylate and 5-40 wt. % of rosuvastatin calcium, and a method for preparing the same.

Chinese Patent Application CN200610028434.8 discloses a pharmaceutical composition comprising a therapeutically effective amount of amlodipine and a therapeutically effective amount of rosuvastatin calcium, and a method for preparing the same.

Although the combination of amlodipine and rosuvastatin could bring both antihypertensive and antilipemic effects as described in the above two patent applications, these effects are not sufficient for hypertensive patients who may have high risk of cardiovascular diseases, as chronic hypertension may result in damages to key organs such as cardiovascular system and kidney. Accordingly, the objective of antihypertensive treatment is not only to reduce the blood pressure to desired level, but also to rectify the coexisting risk factors such as cardiovascular diseases. Meanwhile, a suitable medicament shall be selected to improve metabolic disorders and prognosis of the patients. Therefore, it is desired in clinical treatment to find a multidrug combination therapy which could treat hypertensive diseases, while effectively controlling the incidence of associated cardiovascular diseases, and more potently improving the survival and prognosis of hypertensive patients.

SUMMARY OF THE INVENTION

The objective of the present invention is to provide a novel pharmaceutical composition for treating hypertension or metabolic syndrome, while effectively controlling the incidence of associated cardiovascular diseases, and more potently improving the survival and prognosis of hypertensive patients. While the blood pressure is reduced to desired level by the antihypertensive therapy, the coexisting risk factors such as cardiovascular diseases are rectified, metabolic disorders and prognosis of the patients are improved, and the survival rate of the hypertensive patients is increased.

The present invention provides a pharmaceutical composition, which comprises the following active ingredients:

1) amlodipine or a pharmaceutically acceptable salt thereof;
2) pioglitazone or a pharmaceutically acceptable salt thereof; and
3) rosuvastatin or a pharmaceutically acceptable salt thereof.

In one embodiment of the present invention, the pharmaceutically acceptable salt of amlodipine is selected from besylate, maleate, hydrochloride, formate, acetate, hydrobromate, aspartate, methanesulfonate, sulfate or tartrate.

In one embodiment of the present invention, amlodipine is levo-amlodipine or a mixture of levo-amlodipine and dextro-amlodipine.

In one embodiment of the present invention, the weight ratio of amlodipine or a pharmaceutically acceptable salt thereof, pioglitazone or a pharmaceutically acceptable salt thereof, and rosuvastatin or a pharmaceutically acceptable salt thereof is 1:(0.1~18):(0.1~16), wherein the weight of the pharmaceutically acceptable salt of amlodipine is calculated as amlodipine, the weight of the pharmaceutically acceptable salt of pioglitazone is calculated as pioglitazone, and the weight of the pharmaceutically acceptable salt of rosuvastatin is calculated as rosuvastatin.

Preferably, the weight ratio of amlodipine or a pharmaceutically acceptable salt thereof, pioglitazone or a pharmaceutically acceptable salt thereof, and rosuvastatin or a pharmaceutically acceptable salt thereof is 1:(0.1~9):(0.1~8), wherein the weight of the pharmaceutically acceptable salt of amlodipine is calculated as amlodipine, the weight of the pharmaceutically acceptable salt of pioglitazone is calculated as pioglitazone, and the weight of the pharmaceutically acceptable salt of rosuvastatin is calculated as rosuvastatin.

Preferably, the weight ratio of amlodipine or a pharmaceutically acceptable salt thereof, pioglitazone or a pharmaceutically acceptable salt thereof, and rosuvastatin or a pharmaceutically acceptable salt thereof is 1:(0.1~4.5):(0.1~4), wherein the weight of the pharmaceutically acceptable salt of amlodipine is calculated as amlodipine, the weight of the pharmaceutically acceptable salt of pioglitazone is calculated as pioglitazone, and the weight of the pharmaceutically acceptable salt of rosuvastatin is calculated as rosuvastatin.

In one embodiment of the present invention, the pharmaceutically acceptable salt of pioglitazone in the pharmaceutical composition of the present invention is preferably pioglitazone hydrochloride.

In one embodiment of the present invention, the pharmaceutically acceptable salt of rosuvastatin in the pharmaceutical composition of the present invention is preferably rosuvastatin calcium.

In view of recent progress of clinical research in antihypertensive therapy and the trend of the development of hypertensive diseases, the present invention inventively introduces pioglitazone, an anti-diabetes insulin sensitizer, into the existing antihypertensive therapy and achieves extraordinary treatment effects. The experiments demonstrate that the pharmaceutical composition of the present invention not only exhibits significant antihypertensive benefits, but also effectively reduces the damage to key organs such as cardiovascular system and kidney caused by chronic hypertension, effectively rectifies the coexisting risk factors such as cardiovascular diseases, improves metabolic disorders and prognosis of the patients, and achieves good and unexpected synergistic effects in the treatment and control of various cardiovascular complications caused by hypertension. The determination result of cardiac hypertrophy and carotid intima-media thickness in rats demonstrates that the pharmaceutical composition provided by the present invention can reverse cardiac hypertrophy and effectively control the incidence of cardiovascular diseases, which proves its advantages in prevention and treatment of cardiovascular diseases. Meanwhile, the determination result of urinary microalbumin in rats demonstrates that the pharmaceutical composition of the present invention also has renoprotective effects, and can effectively delay the damage to the kidney of hypertension patients.

It has been confirmed by a great deal of experimental researches that combined administration of one of a mixture of levo-amlodipine and dextro-amlodipine or a pharmaceutically acceptable salt thereof, or the besylate, maleate, hydrochloride, formate, acetate, hydrobromate, aspartate, methanesulfonate, sulfate or tartrate of amlodipine with pioglitazone or a pharmaceutically acceptable salt thereof, and rosuvastatin or a pharmaceutically acceptable salt thereof can also reverse cardiac hypertrophy in rats, exhibit remarkable antihypertensive effects, effectively reduce the damage to key organs such as cardiovascular system and kidney caused by chronic hypertension, effectively rectify the risk factors such as cardiovascular diseases, reduce urinary microalbumin, and protect kidney from damage caused by hypertension. Meanwhile, it can also improve metabolic disorders and exhibit treatment effects in the treatment of metabolic syndrome.

Accordingly, the present invention provides a use of the pharmaceutical composition of the present invention in preparing a medicament for treating hypertension or metabolic syndrome.

The present invention also provides a method for treating hypertension or metabolic syndrome with the pharmaceutical composition of the present invention, which comprises administration of an effective amount of the pharmaceutical composition of the present invention to a patient in need of such treatment.

The present invention also provides a pharmaceutical composition as described above for treating hypertension or metabolic syndrome.

The term "metabolic syndrome" refers to a pathological condition in which several metabolic disorders coexist in one single patient, and includes obesity (abdominal obesity), insulin resistance, impaired glucose regulation, diabetes mellitus, hypertension, dyslipidemia, microalbunminuria and hyperuricemia, etc. The pharmaceutical composition of the present invention can effectively reduce total cholesterol (TC), high-density lipid cholesterol (HDLC), glycated hemoglobin (HbAlC), fasting blood glucose (FBG), fasting insulin (FINS) and fibrinogen (Fg) in patients with metabolic syndrome, effectively control associated symptoms of cardiovascular diseases, and reduce invalidism rate and fatality rate.

The term "effective amount" refers to a dosage of the pharmaceutical composition that could produce desired treatment effects in a patient.

The pharmaceutical composition of the present invention can be formulated into a solid pharmaceutical formulation, such as tablets, capsules, granules, pills, dripping pills, etc., depending on the properties of the drug and the requirements of convenient administration for the patients. Said tablets include general tablets, coated tablets, sugar-coated tablets, film-coated tablets, enteric-coated tablets, effervescent tablets, chewable tablets, multi-layered tablets, disintegrating tablets, dispersible tablets, sublingual tablets, buccal tablets, implant tablets, soluble tablets, sustained-release tablets, etc. The solid pharmaceutical formulation is employed in the present invention since it has the advantages of convenient carrying and usage, simple and feasible administration route, and good compliance of the patients.

In one embodiment of the present invention, the pharmaceutical composition of the present invention may be in the form of, but not limited to, tablets, capsules or granules.

The pharmaceutical composition of the present invention can be formulated following traditional techniques with the addition of traditional additives such as excipients (e.g., lactose, sucrose, glucose, mannose, sorbitol, starch, dextrin, crystalline cellulose, arabic gum, dextran, etc.), lubricants (magnesium stearate, calcium stearate, talc powder, micronized silica gel, boric acid, sodium dodecylsulfate, etc.), binders (hydroxypropyl cellulose, hydroxypropyl methyl cellulose, polyvinylpyrrolidone, polyethylene glycol, etc.), disintegrating agents (low-substituted hydroxypropyl cellulose, carboxymethyl cellulose, carboxymethyl starch, cross-linked polyvinylpyrrolidone, etc.), emulsifiers (bentonite, magnesium hydroxide, aluminum hydroxide, sodium dodecylsulfate, etc.), stabilizers (methyl p-hydroxybenzoate, benzyl alcohol, phenylethyl alcohol, phenol, sorbic acid, dehydroacetic acid, etc.), flavoring agents (sucrose, flavors, aspartame, cyclodextrin, etc.), diluents, etc.

Additionally, the pharmaceutical composition of the present invention can also be formulated into sustained-release tablets according to the requirements of the patients, so as to regulate blood pressure effectively and safely, maintain a relatively stable plasma drug concentration and longer acting term by slow release, and have the advantages of reduced toxicity and side effects and convenient administration.

The sustained-release tablets prepared from the pharmaceutical composition of the present invention uses cellulose derivatives or vinyl polymer as the sustained-release matrix, wherein the matrix may be one or more of methyl cellulose, hydroxymethyl cellulose, hydroxyethyl cellulose, hydroxypropyl cellulose, hydroxypropyl methyl cellulose, carboxymethyl cellulose, carboxyethyl cellulose, microcrystalline cellulose, starch, polyvinylpyrrolidone and acrylic resin.

The advantages of the pharmaceutical composition according to the present invention lie in the following aspects:

1. The present invention inventively introduces pioglitazone, an anti-diabetes insulin sensitizer, or a pharmaceutically acceptable salt thereof into the existing antihypertensive therapy, and achieves very good synergetic antihypertensive effects. The combined administration of amlodipine, a calcium channel blocker (CCB), or a pharmaceutically acceptable salt thereof, with pioglitazone, an HMG-CoA reductase inhibitor, or a pharmaceutically acceptable salt thereof, and rosuvastatin or a pharmaceutically acceptable salt thereof exhibits good synergetic antihypertensive effects in experimental researches and clinical observations.

2. The pharmaceutical composition significantly reduces the incidence and degree of adverse effects. The tri-drug combination administration of an antihypertensive drug+an antihyperglycemic drug+an antilipemic drug results in significant synergetic effect in the treatment of hypertension, which significantly reduces the administration dosage, and significantly reduces the incidence and degree of adverse effects as well.

3. Long-term administration of the pharmaceutical composition of the present invention leads to beneficial effects on the long-term survival rate of hypertension patients. It is the most significative clinical problem addressed by the present invention to provide positive effects on the prognosis of the patients. Traditional antihypertensive drugs do not have good prevention and treatment effects on the complications caused by hypertension, such as brain stocks, kidney damage, coronary heart disease, etc., while the pharmaceutical composition of the present invention can treat hypertension, while effectively control the incidence of associated cardiovascular diseases, further improve the survival and prognosis of hypertension patients, reduce the blood pressure to desired level in the antihypertensive treatment, rectify the coexisting risk factors such as cardiovascular diseases, improve metabolic disorders and prognosis of the patients, and increase the survival rate of hypertension patients.

4. The pharmaceutical composition of the present invention has various applications. Due to the synergetic effect, the present invention is suitable for various types of hypertension patients, especially patients with stroke-prone hypertension and hypertension-combined kidney damage. Additionally, the present invention also exhibits good effects on hypertension-combined coronary heart disease and angina, peripheral vascular disease, senile hypertension, gestational hypertension and resistant hypertension.

5. The pharmaceutical composition of the present invention achieves desired effects in the treatment of metabolic syndrome, which has high morbidity in the current society.

DETAILED DESCRIPTION

Hereinafter, the invention will be explained in more detail with the following examples. However, the scope of the present invention is not limited thereto. Any changes and modifications that are obvious for those skilled in the art are intended to be included within the scope of the present invention. All references cited herein are hereby entirely incorporated to the description by reference.

In the following examples, amlodipine refers to amlodipine or a pharmaceutically acceptable salt thereof, levo-amlodipine refers to levo-amlodipine or a pharmaceutically acceptable salt thereof; the weight of the pharmaceutically acceptable salt of amlodipine is calculated as amlodipine, and the weight of pioglitazone hydrochloride is calculated as pioglitazone.

EXAMPLE 1

Common Tablets

| | |
|---|---|
| Rosuvastatin calcium | 10 g |
| Amlodipine | 10 g |
| Pioglitazone hydrochloride | 15 g |
| Starch | 140 g |
| Dextrin | 120 g |
| 50% Ethanol | Appropriate amount |
| Magnesium stearate | 1.0 g |

Manufacture process: Prescribed amounts of rosuvastatin calcium, amlodipine, pioglitazone hydrochloride, starch and dextrin were weighed and uniformly mixed. To the mixed powder, an appropriate amount of 50% ethanol was added, and uniformly mixed to obtain a soft material, which was allowed to pass through an 18-mesh nylon screen to prepare wet granules. The wet granules were dried at about 60° C. The moisture content of the dried granules should be controlled below 1.5%. The dried granules were further granulated with a 20-mesh screen, uniformly mixed with magnesium stearate and pressed to obtain the final product.

EXAMPLE 2

Capsules

| | |
|---|---|
| Rosuvastatin calcium | 10 g |
| Levo-amlodipine | 10 g |
| Pioglitazone hydrochloride | 10 g |
| Microcrystalline cellulose | 300 g |
| Micronized silica gel | 12 g |

Manufacture process: Prescribed amounts of rosuvastatin calcium, levo-amlodipine, pioglitazone hydrochloride, microcrystalline cellulose and micronized silica gel were weighed and pulverized, screened with a 100-mesh screen, uniformly mixed, and then directly filled into capsules to obtain the final product.

EXAMPLE 3

Double-Layer Tablets

| | |
|---|---|
| Rosuvastatin calcium | 40 g |
| Mannitol | 10 g |
| Lactose | 40 g |
| Microcrystalline cellulose | 20 g |
| 6% PVP in 95% ethanol solution | 120 g |
| Magnesium stearate | 2 g |

Manufacture process a: Rosuvastatin calcium was screened with a 100-mesh screen, and mannitol, lactose and microcrystalline cellulose were screened with an 80-mesh screen. Prescribed amounts of rosuvastatin calcium, mannitol, lactose and microcrystalline cellulose were weighed and uniformly mixed, to which an appropriate amount of 6% polyvinylpyrrolidone (PVP) in 95% ethanol solution was added to prepare granules. The granules were dried at 60° C. and the dried granules were screened with a 16-mesh screen. Prescribed amount of magnesium stearate was added to the dried granules.

| | |
|---|---|
| Amlodipine | 10 g |
| Pioglitazone hydrochloride | 45 g |
| Pregelatinized starch | 50 g |
| Mannitol | 50 g |
| 6% PVP in 95% ethanol solution | 100 g |
| Micronized silica gel | 5 g |

Manufacture process b: Amlodipine and pioglitazone hydrochloride were screened with a 100-mesh screen, and pregelatinized starch and mannitol were screened with an 80-mesh screen. Prescribed amounts of amlodipine, pioglitazone hydrochloride, pregelatinized starch and mannitol were weighed and uniformly mixed, to which an appropriate amount of 6% PVP in 95% ethanol solution was added to prepare granules. The granules were dried at 60° C. and the dried granules were screened with a 16-mesh screen. Prescribed amount of micronized silica gel was added to the dried granules.

The granules manufactured from the manufacture processes a and b were pressed with a double-layer pressing machine to obtain double layer tablets.

EXAMPLE 4

Dispersible Tablets

| | |
|---|---|
| Rosuvastatin calcium | 5 g |
| Levo-amlodipine | 10 g |
| Pioglitazone hydrochloride | 5 g |
| Calcium carboxymethylcellulose | 15 g |
| Crosslinked polyvinylpyrrolidone | 15 g |
| Microcrystalline cellulose | 140 g |
| 10% Starch slurry | Appropriate amount |
| Magnesium stearate | 6 g |

Manufacture process: Prescribed amounts of rosuvastatin calcium, levo-amlodipine and pioglitazone hydrochloride were screened with a 100-mesh screen, and calcium carboxymethylcellulose, crosslinked polyvinylpyrrolidone and microcrystalline cellulose were screened with an 80-mesh screen. The above components were uniformly mixed and an appropriate amount of 10% starch slurry was added to prepare granules. Magnesium stearate was added to the granules and the mixture was pressed to obtain the final product.

EXAMPLE 5

Granules

| | |
|---|---|
| Rosuvastatin calcium | 40 g |
| Amlodipine | 5 g |
| Pioglitazone hydrochloride | 45 g |
| Starch | 200 g |
| Dextrin | 50 g |
| Sucrose powder | 50 g |
| 80% Ethanol | Appropriate amount |

Manufacture process: Prescribed amounts of rosuvastatin calcium, amlodipine, pioglitazone hydrochloride, starch, dextrin and sucrose powder were weighed and uniformly mixed. To the mixed powder, an appropriate amount of 80% ethanol was added, and uniformly mixed to prepare a soft material, which was allowed to pass through an 18-mesh nylon screen to prepare wet granules. The wet granules were dried at about 60° C., finished with a 20-mesh screen, and packaged to obtain the final product.

EXAMPLE 6

Disintegrating Tablets

| | |
|---|---|
| Rosuvastatin calcium | 1 g |
| Levo-amlodipine | 10 g |
| Pioglitazone hydrochloride | 1 g |
| Crosslinked sodium carboxymethylcellulose | 10 g |

-continued

| Microcrystalline cellulose | 100 g |
|---|---|
| Polyvinylpyrrolidone | 20 g |
| 5% PVP in 60% ethanol solution | Appropriate amount |
| Micronized silica gel | 5 g |

Manufacture process: Prescribed amounts of rosuvastatin calcium, levo-amlodipine and pioglitazone hydrochloride were weighed, granulated in a fluidized bed with microcrystalline cellulose as a filler, crosslinked sodium carboxymethylcellulose and polyvinylpyrrolidone as disintegrating agents, 5% PVP in 60% ethanol solution as a binder, and micronized silica gel as a glidant, and then pressed to obtain the final product.

EXAMPLE 7

Sustained Release Tablets

| Rosuvastatin calcium | 10 g |
|---|---|
| Levo-amlodipine | 10 g |
| Pioglitazone hydrochloride | 5 g |
| Hydroxypropylmethyl cellulose | 80 g |
| Polyvinylpyrrolidone | 100 g |
| Lactose | 85 g |
| Micronized silica gel | 100 g |

Manufacture process: Prescribed amounts of rosuvastatin calcium, levo-amlodipine and pioglitazone hydrochloride were uniformly mixed with prescribed amounts of hydroxypropylmethyl cellulose and lactose. Polyvinylpyrrolidone was then added as a binder to prepare granules, which were dried at 40° C. to 80° C. to obtain dried granules. Prescribed amount of micronized silica was added as a lubricant to the dried granules, uniformly mixed, and pressed to obtain the final product.

EXAMPLE 8

Capsules

| Rosuvastatin calcium | 32 g |
|---|---|
| Levo-amlodipine | 2 g |
| Pioglitazone hydrochloride | 36 g |
| Microcrystalline cellulose | 300 g |
| Micronized silica gel | 12 g |

Manufacture process: Prescribed amounts of rosuvastatin calcium, levo-amlodipine, pioglitazone hydrochloride, microcrystalline cellulose and micronized silica gel were pulverized, screened with a 100-mesh screen, uniformly mixed, and then directly filled into capsules to obtain the final product.

EXAMPLE 9

Treatment Effects of the Pharmaceutical Composition of the Present Invention on Blood Pressure and Cardiac Hypertrophy in Spontaneously Hypertensive Rats 1. Experimental Animals and Animal Groups Forty-eight spontaneously hypertensive rats (male, body weight (300±20) g, provided by Pharmacological Center for New Medicine of Shandong New Time Pharmaceutical Co., Ltd.) were fed for one week for acclimation, and then randomly divided into six groups with eight animals in each group.

Model control group: intragastric administration of same volume of physiological saline;

P group: 1 mg/(kg·d) of pioglitazone;

A+R group: 2 mg/(kg·d) of amlodipine+1 mg/(kg·d) of rosuvastatin calcium;

P+R group: 1 mg/(kg·d) of pioglitazone+1 mg/(kg·d) of rosuvastatin calcium;

A group: 2 mg/(kg·d) of amlodipine;

Pharmaceutical composition of the present invention: 2 mg/(kg·d) of amlodipine+1 mg/(kg·d) of pioglitazone+1 mg/(kg·d) of rosuvastatin calcium;

Each group was given intragastric administration once every day for ten weeks. During the experiment, the diet, survival status and behaviors of the animals were recorded, and the animals were weighted once every day and the doses of administration were adjusted according to the body weights. Animals were sacrificed after ten weeks, and their hearts were taken out to determine the weights of left ventricles and calculate left ventricular indexes.

2. Experimental Methods and Results 2.1 Effects of the Pharmaceutical Composition of the Present Invention on the Blood Pressure of Spontaneously Hypertensive Rats Temperature was controlled between 18° C. and 22° C., humidity was controlled between 45% and 65% with natural light indoors. Tail arterial blood pressure of a conscious rat was measured with Intelligent Non-invasive Blood Pressure Monitor BP-2006A (provided by Beijing Softron Co., Ltd.). Blood pressures were measured five times between two and five hours after intragastric administration in the first week, the third week and the sixth week, respectively. The average value of the blood pressures was used as the blood pressure of the sample.

TABLE 1

Effects of the pharmaceutical composition of the present invention on the blood pressure of spontaneously hypertensive rats ($\overline{X} \pm S$, n = 8) (mmHg)

| Groups | Before treatment | After treatment | | |
|---|---|---|---|---|
| | | First week | Third week | Sixth week |
| Model group | 152 ± 8.1 | 158 ± 9.2 | 164 ± 8.7 | 178 ± 9.2 |
| A + R Group | 150 ± 12.3 | 151 ± 10.5 | 152 ± 9.6* | 150 ± 7.0* |
| P group | 151 ± 7.6 | 157 ± 8.6 | 162 ± 10.3 | 170 ± 8.8 |
| P + R group | 149 ± 9.4 | 156 ± 8.9 | 160 ± 9.2 | 165 ± 11.3* |

TABLE 1-continued

Effects of the pharmaceutical composition of the present invention on the blood pressure of spontaneously hypertensive rats ($\bar{X} \pm S$, n = 8) (mmHg)

| Groups | Before treatment | After treatment | | |
|---|---|---|---|---|
| | | First week | Third week | Sixth week |
| A Group | 150 ± 9.0 | 152 ± 9.5 | 154 ± 11.4* | 156 ± 10.9** |
| Pharmaceutical composition of the present invention | 153 ± 13.7 | 149 ± 7.1 | 140 ± 16.2**▼*# | 135 ± 7.6**▼*# |

*p < 0.05, compared with the model group,
**p < 0.01, compared with the model group,
▼p < 0.05, compared with the A group,
*p < 0.05, compared with the P + R group; and
p < 0.05, compared with the A + R group.

The above results indicated that the combination of rosuvastatin, amlodipine and pioglitazone has a synergetic effect on lowering the blood pressure of spontaneously hypertensive rats. As shown from the data of blood pressures measured in the third week and the sixth week, the combined administration of the three drugs exhibited good synergetic effects, no matter the administration of amlodipine and rosuvastatin calcium in combination with pioglitazone, or administration of pioglitazone and rosuvastatin calcium in combination with amlodipine.

2.2. Measurements of Heart Weight, Left Ventricle Weight, Body Weight and Left Ventricular Hypertrophy Index (Left Ventricular Weight/Body Weight):

After being sacrificed with 10% potassium chloride (2 mmol/L, 1 ml/rat), the rats were weighed. Heart was taken out and aortas and connective tissues outside of the heart were removed. The heart was cleaned by washing, dried with a filter paper, and weighted. The left ventricular was weighed after the atria were removed, and a ratio of left ventricular weight to body weight was calculated.

TABLE 2

Effects of the pharmaceutical composition of the present invention on cardiac hypertrophy of spontaneously hypertensive rats ($\bar{X} \pm S$, n = 8) (g)

| Groups | Body weight | Left ventricular weight | Left ventricular weight/body weight ($\times 10^{-3}$) |
|---|---|---|---|
| Model group | 301 ± 12 | 1.06 ± 0.19 | 3.52 ± 0.27 |
| A + R Group | 304 ± 13 | 0.91 ± 0.16* | 2.99 ± 0.15** |
| P group | 298 ± 12 | 0.99 ± 0.10 | 3.33 ± 0.19 |
| P + R group | 308 ± 14 | 0.97 ± 0.13 | 3.15 ± 0.28* |
| A Group | 297 ± 15 | 0.92 ± 0.17 | 3.10 ± 0.15** |
| Pharmaceutical composition of the present invention | 303 ± 14 | 0.75 ± 0.15**▼*# | 2.48 ± 0.25**▼*# |

*p < 0.05, compared with the model group,
**p < 0.01, compared with the model group,
▼p < 0.05, compared with the A group,
*p < 0.05, compared with the P + R group; and
p < 0.05, compared with the A + R group.

The results indicated that the combination of rosuvastatin, amlodipine and pioglitazone could effectively reverse left ventricular hypertrophy in spontaneously hypertensive rats, and combined administration of the three drugs exhibits a good synergetic effect in the treatment of cardiac hypertrophy in spontaneously hypertensive rats. Good synergetic effects could be achieved by administration of amlodipine and rosuvastatin calcium in combination with pioglitazone, or administration of pioglitazone and rosuvastatin calcium in combination with amlodipine.

EXAMPLE 10

Treatment Effects of the Pharmaceutical Composition of the Present Invention on Urinary Microalbumin and Carotid Intima-Media Thickness of the Carotid Arteries in Spontaneously Hypertensive Rats 1. Experimental Animals and Animal Groups Forty-eight spontaneously hypertensive rats (male, body weight (300±20) g, provided by the Pharmacological Center for New Medicine of Shandong New Time Pharmaceutical Co., Ltd.) were fed for one week for acclimation, and then randomly divided into six groups with eight rats in each group.

Model control group: intragastric administration of same volume of physiological saline;

P group: intragastric administration of 2 mg/(kg·d) of pioglitazone;

LA+R group: intragastric administration of 1 mg/(kg·d) of levo-amlodipine+1 mg/(kg·d) of rosuvastatin calcium;

P+R group: intragastric administration of 2 mg/(kg·d) of pioglitazone+1 mg/(kg·d) of rosuvastatin calcium;

LA group: intragastric administration of 1 mg/(kg·d) of levo-amlodipine;

Pharmaceutical composition of the present invention: intragastric administration of 1 mg/(kg·d) of levo-amlodipine+2 mg/(kg·d) of pioglitazone+1 mg/(kg·d) of rosuvastatin calcium;

Each group was given intragastric administration once every day and fed with high sugar and high fat diets for six months. During the experiment, the diet, survival status and behaviors of the animals were recorded, and the animals were weighed once every week and the doses of administration were adjusted according to the body weights.

2. Experimental Methods and Results 2.1. Measurements of Urinary Microalbumin:

Reagents:

1. 10% (v/v) glacial acetic acid solution (pH 2.8).

2. 0.303 mol/L glycine-glacial acetic acid buffer solution (pH 3.0): 22.72 g of glycine was weighed and diluted with 10% glacial acetic acid solution to 1000 ml, to which 100 mg of $NaN_3$ was added. The buffer solution can be kept for one year at room temperature after sealed.

3. Bromophenol blue (1.924 mmol/L) stock solution: 257.36 mg of BPB was precisely weighed and dissolved to 200 ml with absolute ethanol. The stock solution can be kept for one year in a refrigerator at 4° C.

4. Bromophenol blue (0.231 mmol/L) developing agent: to 60 ml of BPB stock solution, 2.5 ml Triton X-100 was added, and then diluted to 500 ml with glycine-glacial acetic acid buffer solution. The developing agent can be kept for one year at room temperature after sealed.

Collection and detection of samples: rats were taken out and fed in a metabolic cage at the fourth week, the eighth week, the twelfth week and the sixteenth week, respectively, and twelve-hour overnight urinary collection was performed. Urinary amounts were precisely recorded. 4 ml of urine was sampled, treated with sodium azide, and centrifuged at 2000 r/min for 10 min. Supernatant was collected and stored in a freezer at −20° C. before urinary albumin measurement. 2 ml of stored urine of rat was sampled, and 1 ml developing agent was added and uniformly mixed (avoiding the generation of air bubbles). The absorbance A was determined with a UV spectrophotometer at 600 nm.

TABLE 3

Effects of the pharmaceutical composition of the present invention on urinary microalbumin in spontaneously hypertensive rats ($\overline{X} \pm S$)

| Groups | n | Absorbance A (600 nm) |
|---|---|---|
| Model group | 8 | 0.687 ± 0.216 |
| A + R Group | 8 | 0.603 ± 0.232 |
| P group | 8 | 0.568 ± 0.125* |
| P + R group | 8 | 0.575 ± 0.161* |
| A Group | 8 | 0.617 ± 0.177 |
| Pharmaceutical composition of the present invention | 8 | 0.411 ± 0.158** |

*$p < 0.05$, compared with the model group,
**$p < 0.01$, compared with the model group.

The results indicated that the combination of rosuvastatin, levo-amlodipine and pioglitazone could decrease urinary microalbumin and protect kidney from the damage caused by hypertension, and exhibited desired effects. Good synergetic effects on urinary microalbumin of spontaneously hypertensive rats were achieved either by administration of levo-amlodipine and rosuvastatin calcium in combination with pioglitazone, or by administration of pioglitazone and rosuvastatin calcium in combination with levo-amlodipine.

2.2. Measurements of Carotid Intima-Media Thickness of the Carotid Arteries

After the animal was anesthetized and fixed, Even's blue (60 mg/kg) dye was injected via a femoral artery. After 30 minutes, myocardial perfusion was performed with 0.9% physiological saline as a perfusate at a perfusion pressure of 13.3 kPa until the effluent became clear. Then, 4% paraformaldehyde in physiological saline was perfused for 10 minutes for in situ fixation (the perfusion pressure was the same as above). The section of Even's blue-stained carotid artery was taken and further fixed with formalin solution, and three parts, i.e. the front, the middle and the rear parts, respectively, were sampled and embedded in paraffin, and then sliced discontinuously to obtain 8 to 10 layers, which were stained with HE. Three vascular sections were randomly selected and input into a computer image processing system so as to perform a computerized image measurement, thereby calculating the maximum intima thickness, the intima-media thickness, and the ratio of the intima to media thickness.

TABLE 4

Effects of the pharmaceutical composition of the present invention on intima-media thickness in spontaneously hypertensive rats ($\overline{X} \pm S$, n = 8)

| Groups | Maximum intima thickness (mm) | Ratio of intima to media thickness |
|---|---|---|
| Model group | 0.142 ± 0.031 | 2.432 ± 0.456 |
| A + R Group | 0.094 ± 0.025* | 1.683 ± 0.328* |
| P group | 0.130 ± 0.026 | 2.246 ± 0.361 |
| P + R group | 0.110 ± 0.028* | 1.923 ± 0.422* |
| A Group | 0.116 ± 0.030* | 2.125 ± 0.357* |
| Pharmaceutical composition of the present invention | 0.062 ± 0.014**▼*# | 1.102 ± 0.243**▼*# |

*$p < 0.05$, compared with the model group,
**$p < 0.01$, compared with the model group,
▼$p < 0.01$, compared with the A group,
*$p < 0.05$, compared with the P + R group; and
$p < 0.05$, compared with the A + R group.

The results indicated that the combination of rosuvastatin, levo-amlodipine and pioglitazone could effectively improve the intima-media thickness in spontaneously hypertensive rats, and had a good synergetic effect on the carotid intima-media thickness of carotid in spontaneously hypertensive rats. Good synergetic effects were achieved by administration of levo-amlodipine and rosuvastatin calcium in combination with pioglitazone, or by administration of pioglitazone and rosuvastatin calcium in combination with levo-amlodipine.

EXAMPLE 11

Treatment Effects of the Pharmaceutical Composition of the Present Invention on Patients Suffered from Metabolic Syndrome 1. General Information Eighty-eight metabolic syndrome patients were selected from those received treatment in Linyi People's Hospital from May 2007 to May 2008, and randomly divided into a control group and an experimental group.

Control group: twenty-eight males and sixteen females, whose ages were between 62 and 71 and whose body mass indexes (BMI) were between 25.5 and 30;

Experimental group: twenty-four males and twenty females, whose ages were between 60 and 70 and whose body mass indexes (BMI) were between 24.5 and 31;

Before the treatment, all patients were subjected to blood lipids (including total cholesterol (TC), high-density lipid cholesterol (HDLC)) analysis, and detection of glycated hemoglobin (HbAlC), fasting blood glucose (FBG), fasting insulin (FINS) and fibrinogen (Fg).

Patients suffered from metabolic syndrome were selected according to the diagnostic standards for type-II diabetes mellitus and hypertension made by WHO in 1999 and referring to the diagnostic standards for metabolic syndrome made by US National Cholesterol Education Program Adult Treatment Panel (NCEP-ATP III) in 2000, while cases of primary hypertension, heart failure (above grade II), diseases in liver, kidney and blood system and like were excluded.

2. Treatment Strategy:

Patients in the control group were administrated with 15 mg of pioglitazone once every day, and patients in the experimental group were administrated with 5 mg of amlodipine, 7.5 mg of pioglitazone and 5 mg of rosuvastatin calcium, i.e. the proportions as described in Example 1, once every day. After eight weeks of continuous treatment, all of the above parameters were re-determined, in which blood glucose was determined with hexokinase method, blood lipid was determined with esterase method, fibrinogen was determined with coagulation method and chromogenic substrate assay, HbAlC was determined with chromatography, and fasting insulin was determined with chemiluminescence immunoassay.

Statistical analysis: SPSS software was employed, and test of significance was performed by using a paired sample t test.

3. Treatment Results:

TABLE 5

Changes of Fg, FINS, HbA1C and TC/HDLC before and after treatment
(X̄ ± S)

| Parameters | Before treatment | | After treatment | |
|---|---|---|---|---|
| | Control group | Experimental group | Control group | Experimental group |
| FBG (mmol/L) | 7.12 ± 2.06 | 7.08 ± 2.13 | 6.63 ± 1.65 | 6.04 ± 1.38*# |
| FINS (mIU/L) | 32.4 ± 7.21 | 31.6 ± 8.32 | 25.68 ± 5.34 | 19.48 ± 5.10*# |
| HbAlC (%) | 6.89 ± 0.65 | 6.93 ± 0.62 | 6.39 ± 0.56 | 5.87 ± 0.52*# |
| TC/HDLC (mmol/L) | 4.11 ± 1.26 | 4.08 ± 1.22 | 3.75 ± 0.84 | 3.32 ± 0.67*# |
| Fg (mg/dl) | 419.6 ± 89.62 | 425.0 ± 84.37 | 392.6 ± 64.51 | 347.3 ± 58.46*# |

*$p < 0.05$, compared with the experimental group before treatment; and
$p < 0.05$, compared with the control group after treatment.

It can be seen from Table 5 that the values of FBG FINS, HbAlC, TC/HDLC and Fg in the patients suffered from metabolic syndrome before and after treatment with pharmaceutical composition of the present invention show significant differences. Compared with the pioglitazone group, the values of FBG, FINS, HbAlC, TC/HDLC and Fg after treatment with pharmaceutical composition of the present invention also show significant differences. These results indicated that the pharmaceutical composition of the present invention has a reliable and significant treatment effect on metabolic syndrome.

I claim:

1. A pharmaceutical composition, wherein the pharmaceutical composition comprises the active ingredients consisting of:
   1) amlodipine or a pharmaceutically acceptable salt thereof;
   2) pioglitazone or a pharmaceutically acceptable salt thereof; and
   3) rosuvastatin or a pharmaceutically acceptable salt thereof;
   wherein the weight ratio of amlodipine or a pharmaceutically acceptable salt thereof, pioglitazone or a pharmaceutically acceptable salt thereof, and rosuvastatin or a pharmaceutically acceptable salt thereof is 1: (0.1-4.5) : (0.1-4), and the weight of the pharmaceutically acceptable salt of amlodipine is calculated as amlodipine, the weight of the pharmaceutically acceptable salt of pioglitazone is calculated as pioglitazone, and the weight of the pharmaceutically acceptable salt of rosuvastatin is calculated as rosuvastatin.

2. The pharmaceutical composition according to claim 1, wherein the pharmaceutically acceptable salt of amlodipine is selected from besylate, maleate, hydrochloride, formate, acetate, hydrobromate, aspartate, methanesulfonate, sulfate or tartrate.

3. The pharmaceutical composition according to claim 1, wherein amlodipine is levo-amlodipine or a mixture of levo-amlodipine and dextro-amlodipine.

4. The pharmaceutical composition according to claim 1, wherein the pharmaceutical composition is in a solid dosage form.

5. A method for treating hypertension, comprising the administration of an effective amount of the pharmaceutical composition according to claim 1 to a patient in need thereof.

6. The pharmaceutical composition according to claim 2, wherein the pharmaceutical composition is in a solid dosage form.

7. The pharmaceutical composition according to claim 3, wherein the pharmaceutical composition is in a solid dosage form.

8. The pharmaceutical composition according to claim 1, wherein the pharmaceutical composition is in a solid dosage form.

9. A method for treating hypertension, comprising the administration of an effective amount of the pharmaceutical composition according to claim 2 to a patient in need thereof.

10. A method for treating hypertension, comprising the administration of an effective amount of the pharmaceutical composition according to claim 3 to a patient in need thereof.

* * * * *

UNITED STATES PATENT AND TRADEMARK OFFICE
CERTIFICATE OF CORRECTION

Page 1 of 1

PATENT NO.       : 8,722,697 B2
APPLICATION NO.  : 13/055175
DATED            : May 13, 2014
INVENTOR(S)      : Zhiquan Zhao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 251 days.

Signed and Sealed this
Fifteenth Day of September, 2015

Michelle K. Lee
*Director of the United States Patent and Trademark Office*